United States Patent [19]

Cullis et al.

[11] 4,216,770

[45] Aug. 12, 1980

[54] SICKLE CELL THERAPEUTIC TREATMENT

[75] Inventors: Herbert M. Cullis, Silver Spring, Md.; Evelyn E. Dorsey, Washington, D.C.

[73] Assignee: Baxter Travenol Laboratories, Inc., Deerfield, Ill.

[21] Appl. No.: 10,941

[22] Filed: Feb. 9, 1979

[51] Int. Cl.$^2$ .................. A61M 5/00; B01D 21/26
[52] U.S. Cl. ........................... 128/214 R; 233/1 R; 210/DIG. 23
[58] Field of Search ............... 128/214 R; 233/1 R; 210/DIG. 23, 22, 23

[56] References Cited

U.S. PATENT DOCUMENTS

| | | | |
|---|---|---|---|
| 2,876,769 | 3/1959 | Cordova | 128/214 R |
| 3,462,361 | 8/1969 | Greenwalt et al. | 210/23 |
| 3,489,145 | 1/1970 | Judson et al. | 128/214 R |
| 3,833,724 | 9/1974 | Cerami et al. | 424/129 |
| 3,856,624 | 12/1974 | Kraus et al. | 195/1.8 |
| 4,048,325 | 9/1977 | Packer et al. | 424/298 |
| 4,151,844 | 4/1979 | Cullis et al. | 128/214 R |

OTHER PUBLICATIONS

*Carbamyl Phosphate Mediated Inhibition of the Sickling of Erythrocytes in Vivo,* Kraus et al., Biochemical and Biophysical Research Communications, vol. 44, No. 6, 1971, pp. 1381-1387.

*Primary Examiner*—William E. Kamm
*Assistant Examiner*—Thomas J. Wallen
*Attorney, Agent, or Firm*—H. W. Collins; Paul C. Flattery; George H. Gerstman

[57] ABSTRACT

A sickle cell therapeutic treatment is provided by means of continuous flow red blood cell carbamylation. In a substantially continuous process, whole blood is removed from a patient and is directed to a red cell separator chamber of a seal-less type centrifuge. The whole blood is centrifuged and the red blood cells to be treated are removed from the red cell separation chamber and are directed to a reaction chamber. An anti-sickle agent, such as cyanate solution, is introduced into the reaction chamber and is mixed with the red blood cells to be treated. The mixed anti-sickle agent and red blood cells are transferred to a wash chamber in the centrifuge where they are washed, by centrifugation, and the washed, treated red blood cells are combined with the plasma that was separated in the red cell separation chamber and the combination is returned to the patient.

9 Claims, 2 Drawing Figures

SICKLE CELL THERAPEUTIC TREATMENT

BACKGROUND OF THE INVENTION

This invention concerns a novel system for treating sickle cell disease and, more particularly, a substantially continuous system for carbamylating red blood cells to therapeutically treat sickle cell disease.

Sickle cell disease concerns a human blood disorder in which the red blood cells contain hemoglobin S, which is an abnormal hemoglobin. On occasion, the hemoglobin S cells change from the normal disc shape to a crescent shape, and these cells are designated sickle cells. There are presently certain known methods of treating sickle cell disease with an extracorporeal carbamylation method.

One prior art method of treating sickle cell disease by carbamylating red blood cells utilizes a batch process by which a predetermined amount of whole blood is removed from the patient, the whole blood is treated and thereafter the treated blood is reinfused. This prior art method requires the steps of erythropheresing the patient with blood bags, separating the red blood cells with centrifugation and carbamylating the cells by short incubation with an anti-sickle agent, such as a cyanate solution, washing the otherwise toxic carbamylating agent with manual centrifugation and decanting, reconstituting the carbamylated cells with plasma, reinfusing the reconstitate, and repeating this batch process as many times as possible during one day.

In the batch processing described in U.S. Pat. No. 3,833,724, a unit of the patient's blood is removed into a bag containing acid-citrate-dextrose (ACD). The blood is then centrifuged and the plasma is returned to the patient. The recovered red cells are incubated with an aqueous solution of sodium cyanate (0.001 M to 0.01 M) at about 37° C. for about one to two hours. The cells are then washed to remove any unreacted cyanate and the resulting carbamylated cells are then reintroduced into the patient.

The aforesaid type of batch treatment process is labor intensive and time consuming. Typically, no more than three patients can be treated in one day at one blood treatment center. Because of the batch nature of the process, patients are treated relatively inefficiently, typically having less than 20 percent of their cells carbamylated. The process is merely a treatment that prevents sickling of those cells which have been carbamylated. As these cells age and deteriorate, they are replaced by new sickle-able cells which must then be likewise treated.

We have discovered that a continuous sickle cell treatment process would increase the efficiency of treating sickle cell disease. While in the batch processing extracorporeal blood volumes must be kept low, this problem is overcome using continuous processing.

It is, therefore, an object of the present invention to provide a novel system for treating sickle cell disease utilizing continuous flow red blood cell carbamylation.

Another object of the present invention is to provide a red blood cell carbamylation process that is simple in operation and does not require the removal of substantial extracorporeal blood volumes.

A further object of the present invention is to provide a continuously flowing centrifugal system to partition red blood cells to be treated from the whole blood of a sickle cell patient, and to treat the red blood cells with anti-sickle agents, to wash these agents from the red blood cells and to finally return the red blood cells to the patient.

Other objects and advantages of the present invention will become apparent as the description proceeds.

SUMMARY OF THE INVENTION

In accordance with the present invention, a process is provided for treating sickle cell disease including the step of withdrawing whole blood substantially continuously from a patient. During the withdrawal of the whole blood, the whole blood is directed to a red cell separator, red blood cells to be treated are separated from the plasma by centrifugation, the centrifuged, separated red blood cells to be treated are directed to a reaction chamber, an anti-sickle agent is introduced into the reaction chamber and is mixed with the red blood cells to be treated, the mixture is directed to a wash chamber, a washing medium is introduced into the wash chamber and the mixture is washed by centrifugation, and the washed, treated red blood cells are removed from the centrifuge and are directed back to the patient.

In the illustrative embodiment, the plasma is separated from the red blood cells and the plasma is directed back to the patient. The red blood cells to be treated are also separated in the red cell separator from the white cells and platelets.

In the illustrative embodiment of the present invention, a seal-less centrifuge is provided having a red cell separation chamber and a separate wash chamber. Means are provided for pumping a patient's whole blood to the red cell separation chamber. A plasma removal conduit is coupled to the red cell separation chamber and a red blood cell removal conduit is also coupled to the red cell separation chamber. Means are provided for pumping the red blood cells in the red blood cell removal conduit to a reaction chamber.

Means are provided for introducing an anti-sickle agent to the reaction chamber whereby the anti-sickle agent and the red blood cells are mixed in the reaction chamber. Means are provided for removing the mixture from the reaction chamber and for pumping the mixture into a wash chamber. A washing medium is introduced to the wash chamber and a conduit is provided for removing the washed, treated red blood cells and for directing the washed and treated red blood cells back to the patient.

In the illustrative embodiment, the red blood cell removal conduit is coupled to a location within the red cell separation chamber that substantially prevents removal of white cells and platelets. To this end, the red cell removal conduit is located within the red cell separation chamber at a position generally below the location at which the white cells and platelets are collected during centrifugation.

A more detailed explanation of the invention is provided in the following description and claims, and is illustrated in the accompanying drawings.

DETAILED DESCRIPTION OF THE ILLUSTRATIVE EMBODIMENT

Figure 1:
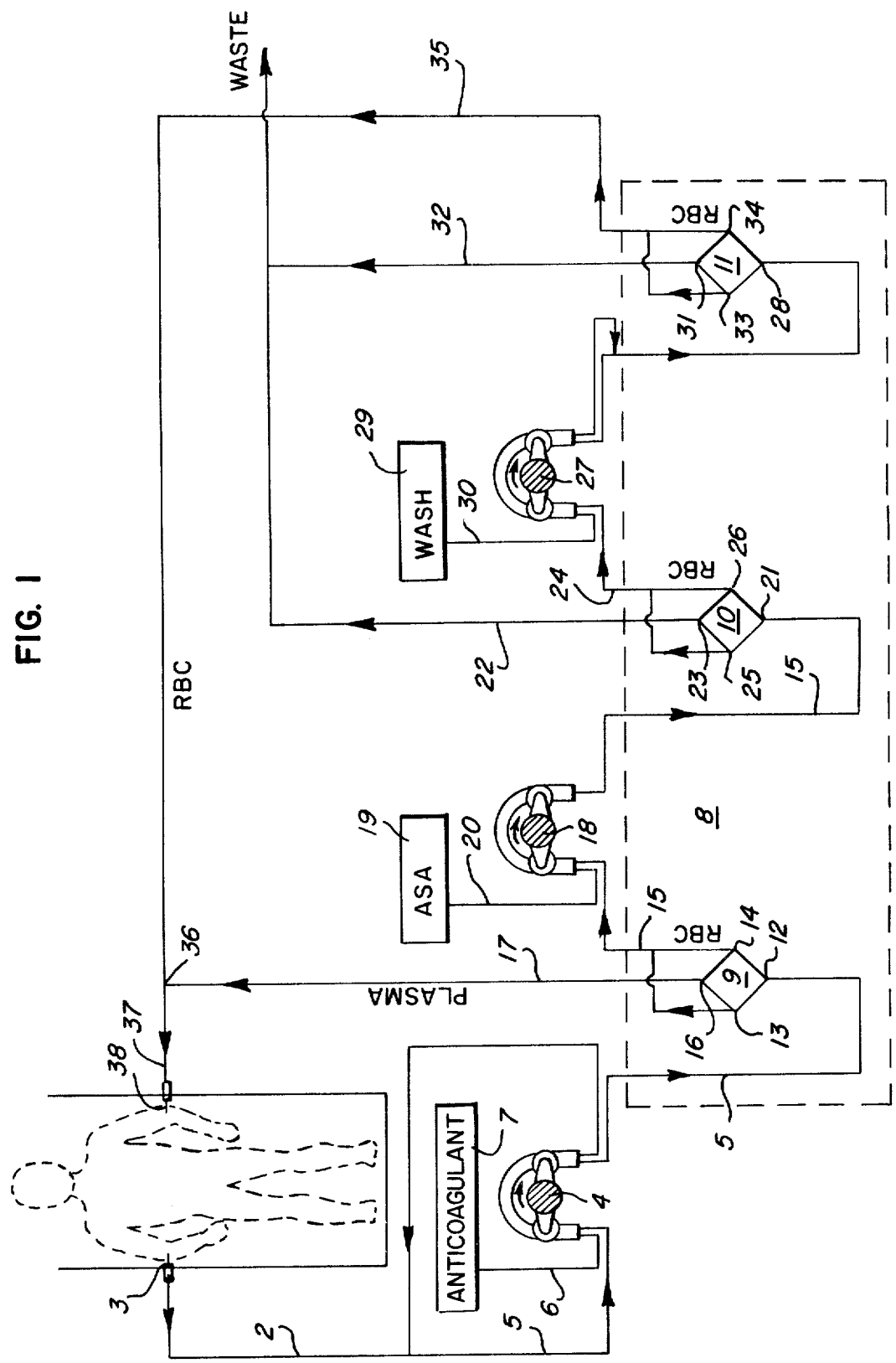
FIG. 1 is a flow diagram of a sickle cell therapeutic treatment system constructed in accordance with the principles of the present invention.

Referring to the drawings, a sickle cell therapeutic treatment system is shown therein in which whole blood is withdrawn from a patient 1 via flexible plastic tubing 2 which is coupled to the vein of the patient by means of a conventional needle assembly 3. The blood is pumped by a peristaltic pump 4 which operates on tubing 5 and which also pumps an anti-coagulant solution in tubing 6 from a source 7 of anti-coagulant solution. As illustrated, the anti-coagulant solution is pumped to mix with the whole blood in tubing 5.

In the drawings, the portion within the dashed lines represents the portion within the rotor assembly 8 of a centrifuge. Thus the centrifuge rotor assembly 8 is multi-chambered and includes a red cell separation chamber 9, a reaction chamber 10 and a wash chamber 11. Each of these chambers may comprise a flexible bag or a rigid container having inlet and outlet ports which are strategically located to enable the receipt of or removal of predetermined fractions of the centrifugate.

Thus the whole blood, with anti-coagulant added, which is flowing in line 5 is coupled to a lower portion 12, preferably the bottom port of red cell separation chamber or bag 9. Side ports 13 and 14 of chamber or bag 9 are coupled to outlet tubing 15 which removes the red blood cells to be treated while an upper port 16 is coupled to tubing 17 which carries the plasma.

During centrifugation, the plasma, which is the least dense, will be located adjacent the top of chamber 9, and the red blood cells that are most desired to be carbamylated will be adjacent the bottom of chamber 9 because they have a higher specific gravity than those red blood cells in which carbamylation is undesired, such as the red blood cells that include granulocytes, lymphocytes, reticulocytes, and platelets. If desired, tubing 17 could be located with respect to chamber 9 so that tubing 17 would collect and transport the plasma and less dense red blood cells, including the red blood cells having granulocytes, lymphocytes, reticulocytes and platelets, and the white blood cells.

The red blood cells to be treated flow in tubing 15 and are pumped by peristaltic pump 18 to reaction chamber 10. A solution of anti-sickle agent 19 is pumped via line 20 by peristaltic pump 18 and is mixed with the red blood cells to be treated.

In the illustrative embodiment, reaction chamber 10 is located within centrifuge rotor assembly 8 so that the anti-sickle agent and the red blood cells to be treated are mixed through centrifugation. The mixing is enhanced by introducing the cells and anti-sickle agent at the bottom 21 of reaction chamber 10, which reaction chamber could comprise a solution bag or rigid container. The anti-sickle agent or the carbamylating agent may be a cyanate solution or any other type of anti-sickle agent that is known in the art, with it being understood that the specific type of carbamylating agent is not considered as part of the invention.

The waste is withdrawn via tubing 22 which is coupled at an upper portion 23 of reaction chamber 10, while the treated red blood cells are withdrawn via tubing 24 that is connected to ports 25, 26, which are at a lower level of the reaction chamber 10.

A peristaltic pump 27 pumps the treated red blood cells in tubing 24 to a lower port 28 of wash chamber 11. A wash solution 29 is pumped by peristaltic pump 27 via tubing 30 to mix in line 24 and thus mix with the treated red blood cells. The waste is withdrawn from an upper port 31 of chamber 11 via tubing 32 while the washed, treated red blood cells are withdrawn from middle level ports 33, 34 via tubing 35. The washed, anti-sickle agent-treated red blood cells which flow in tubing 35 meet, at junction 36, the plasma that is flowing in tubing 17, for return to the patient via tubing 37 and needle assembly 38.

Figure 2:
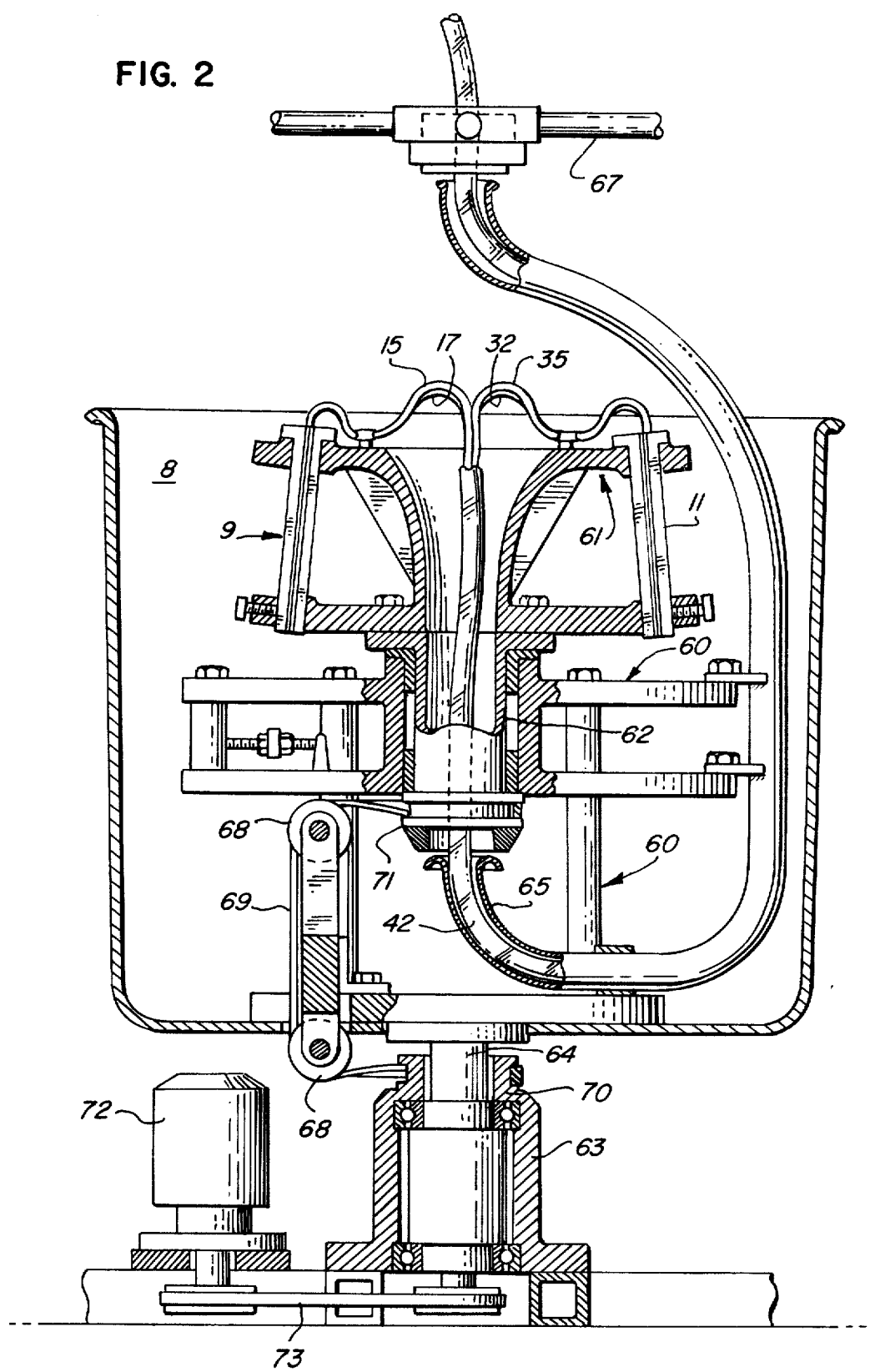
FIG. 2 is an elevational view, taken partly in cross-section, of a seal-less centrifuge used in accordance with the present invention.

Referring to FIG. 2, the sickle cell treatment system of the invention may be utilized in conjunction with a seal-less centrifugation apparatus such as that described in U.S. Pat. No. 4,113,173 or as described in the co-pending application of Herbert M. Cullis and James H. De Vries, Ser. No. 843,296, filed Oct. 18, 1977, and assigned to the present assignee. It is preferred that a seal-less centrifuge be used to alleviate leakage and contamination problems.

The centrifugation apparatus of FIG. 2 includes a rotor drive assembly 60 to which a rotor assembly or carriage 61 is journaled by means of a hollow support shaft 62. The rotor drive assembly 60 is itself journaled to a stationary hub assembly 63 by means of a vertical drive shaft 64. A guide sleeve 65 is mounted on the rotor drive assembly.

The red cell separation chamber 9 and the wash chamber 11 of the treatment system are seated on the rotor assembly 61. If desired, reaction chamber 10 could also be seated on rotor assembly 61. Fluid communication is established between the chambers, which rotate with the rotor assembly, and the non-rotating portions of the processing system, by means of the umbilical cable 42 which is seen to extend from a central location along the axis of rotation of the rotor downwardly through the center of the drive shaft 62, radially outwardly through guide sleeve 65, and upwardly to a fixed axially aligned position established by a support arm 67. Umbilical cable 42 includes plasma removal conduit 17, red cell removal conduit 15, waste removal conduits 22 and 32, and conduits 24 and 35.

The routing of the umbilical cable 42, together with the rotor assembly 61 and rotor drive assembly 60 being driven in the same direction with a speed ratio of 2:1, establishes fluid communication with chambers 9 and 11 without the cable becoming twisted. Instead, the umbilical cable is subjected only to flexing, or repeated partial twists about its axis through angles not in excess of 180 degrees, as the rotor assembly 61 rotates.

A 2:1 speed ratio is obtained between the rotor and rotor drive assembly by means of two pairs of idler pulleys 68 mounted on rotor drive assembly 60 and a drive belt 69. The drive belt is routed over these pulleys and into engagement with a stationary ring-type pulley 70 mounted on hub 63 at one end, and a rotor drive pulley 71 carried on the bottom end of the rotor drive shaft 62 at its other end. As the rotor drive assembly 60 is rotated clockwise by means of a motor 72 and drive belt 73 driving drive shaft 64, drive belt 69 establishes a clockwise rotation of rotor assembly 61. Assuming that stationary pulley 70 and rotor drive pulley 71 have the same diameter, the rotational speed of rotor assembly 61 will be exactly twice that of rotor 60 by reason of the combined effect of the direct 1:1 drive relationship of pulleys 70 and 71 and the planetary motion of pulleys 68 about the axis of rotation of rotor drive assembly 61.

The sickle cell treatment system of the invention may be manufactured as a single disposable unit in which umbilical cable 42 is included. To install this system in the apparatus, the free end of the umbilical cable may be threaded downwardly from support arm 67 through the hollow support sleeve 65 and then upwardly through the hollow rotor support shaft 62. The other end of the cable is then connected to the other components of the system. Since the system remains sealed when installed, all possibility of compromising the sterility of the system is avoided. After use, the entire flow system may be removed from the apparatus and disposed of.

The processing can be operated continuously with the maximum patient time being approximately four hours at a process rate of 30 ml per minute. Using this process, the cells may be subjected to approximately two atmospheres of pressure at approximately 20° to 25° C. Under these conditions, the solubility of oxygen in fluids is substantial, which is believed to inhibit sickling during treatment. Carbamylation may be performed in chamber or bag 10 with the centrifuge rotor assembly 8 in an elutriation process with the carbamylating agent being the elutrient. Incubation times may be relatively short, with approximately two minutes residence time within the chamber being adequate.

Although an illustrative embodiment of the invention has been shown and described, it is to be understood that various modifications and substitutions may be made by those skilled in the art without departing from the novel spirit and scope of the present invention.

What is claimed is:

1. A process for treating sickle cell disease including the step of withdrawing whole blood substantially continuously from a patient and during said withdrawal of said whole blood performing the following steps:
   directing the whole blood to a red cell separator;
   separating red blood cells to be treated from said plasma by centrifugation;
   directing the centrifuged separated red blood cells to be treated to a reaction chamber;
   introducing an anti-sickle agent into said reaction chamber and mixing the anti-sickle agent with the red blood cells to be treated;
   directing red blood cells mixed with the anti-sickle agent to a wash chamber;
   introducing washing medium into the wash chamber and washing by centrifugation the red blood cells mixed with the anti-sickle agent;
   removing the washed red blood cells from the centrifuge and directing the washed, treated red blood cells back to the patient.

2. A process as described in claim 1, including the step of separating the plasma from the red blood cells to be treated and directing the plasma back to the patient.

3. A process as described in claim 2, including the step of mixing the plasma directed back to the patient with the washed, treated red blood cells.

4. A process as described in claim 1, including the step of separating said red blood cells to be treated from the white cells and platelets.

5. A process as described in claim 1, including the step of removing waste from the reaction chamber and the wash chamber.

6. A process as described in claim 1, including the step of introducing an anti-coagulant to the whole blood before the blood cells to be treated are separated from the plasma.

7. A process as described in claim 1, including the step of directing to the reaction chamber substantially only cells that are free of granulocytes, lymphocytes, reticulocytes and platelets.

8. A process for treating sickle cell disease including the step of withdrawing whole blood substantially continuously from a patient and during said withdrawal of said whole blood performing the following steps:
   directing the whole blood to a red cell separator;
   introducing an anti-coagulant to the whole blood;
   separating red blood cells to be treated from said plasma by centrifugation;
   directing the plasma back to the patient;
   directing the centrifuged, separated red blood cells to be treated to a reaction chamber;
   introducing an anti-sickle agent into said reaction chamber and mixing the anti-sickle agent with the red blood cells to be treated;
   directing red blood cells mixed with the anti-sickle agent to a wash chamber;
   introducing washing medium into the wash chamber and washing by centrifugation the red blood cells mixed with the anti-sickle agent;
   removing the washed red blood cells from the centrifuge and directing the washed, treated red blood cells back to the patient;
   removing waste from the reaction chamber and the wash chamber; and
   mixing the plasma directed back to the patient with the washed, treated red blood cells directed back to the patient.

9. A process as described in claim 8, including the step of directing to the reaction chamber substantially only cells that are free of granulocytes, lymphocytes, reticulocytes and platelets.

* * * * *